United States Patent [19]
Ochsner

[11] 4,426,321
[45] Jan. 17, 1984

[54] ODORANT ALKADIENYL KETONES, ALCOHOLS AND OXIMES

[75] Inventor: Paul A. Ochsner, Geneva, Switzerland

[73] Assignee: Givaudan Corporation, Clifton, N.J.

[21] Appl. No.: 286,313

[22] Filed: Jul. 24, 1981

[30] Foreign Application Priority Data

Aug. 8, 1980 [CH] Switzerland ........................ 6019/80
Jun. 15, 1981 [CH] Switzerland ........................ 3913/81

[51] Int. Cl.³ .......................... A61K 7/00; C11B 9/00; C07C 33/02; C07C 49/203
[52] U.S. Cl. ............................... 252/522 R; 564/253; 564/268; 564/259; 564/509; 560/174; 568/417; 568/393; 568/890; 568/878; 424/65; 424/73; 252/174.11; 252/132
[58] Field of Search ................. 564/253; 258, 259; 509 560/174; 568/417, 393, 840, 878; 424/65, 73; 252/522 R, 174.11, 132

[56] References Cited

U.S. PATENT DOCUMENTS 3,637,533  1/1972  Dahill ............................ 252/522 R
4,066,710  1/1978  Ochsner .

FOREIGN PATENT DOCUMENTS 2363535  7/1974  Fed. Rep. of Germany ... 252/522 R
2432351  1/1975  Fed. Rep. of Germany ... 252/522 R
1305994  9/1962  France ............................ 252/522 R
53/18507 2/1978  Japan ............................. 252/522 R
1016249  1/1966  United Kingdom ................ 564/253
1461149  1/1977  United Kingdom ............ 252/522 R
1461150  1/1977  United Kingdom ............ 252/522 R

OTHER PUBLICATIONS

Arctander, *Perfume and Flavor Chemicals*, vol. 2, 1969, No. 2389, Monclair, N.J.
Fieser & Fieser, *Reagents for Organic Synthesis*, 1967, pp. 581, 582, 584 and 1049, John Wiley and Sons, Inc., New York, N.Y.

*Primary Examiner*—Natalie Trousof
*Assistant Examiner*—Raymond Covington
*Attorney, Agent, or Firm*—Robert F. Tavares

[57] ABSTRACT

This invention discloses a number of novel odorant alkadienyl ketones, alcohols and oximes having from 9 to 15 carbon atoms, processes for making same and odorant compositions containing same.

35 Claims, No Drawings

ODORANT ALKADIENYL KETONES, ALCOHOLS AND OXIMES

THE INVENTION

This invention is concerned with novel compounds of the formula

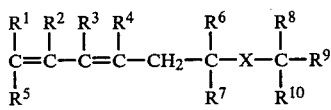

wherein:

(i) X stands for

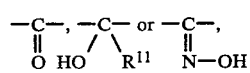

(ii) $R^1$ through $R^{11}$ are alike or different and are selected from the group consisting of hydrogen, methyl, ethyl, n-propyl and isopropyl except that when both $R^6$ and $R^7$ are hydrogen, none of the groups $R^8$, $R^9$ or $R^{10}$ is hydrogen, and (iii) the total number of carbon atoms in the molecule does not exceed fifteen.

The invention is also comcerned with processes for the manufacture of these compounds and their use as odorants.

Formula I is intended to embrace the steriosomers which can occur as a result of cis- or trans-configuration at the C=C and C=N double bonds.

Of the alkyl groups (methyl, ethyl, n-propyl or isopropyl) the methyl group is preferred.

The invention is also concerned with a process for the manufacture of the compounds of formula I. The process of this invention is characterised in that a compound of the formula

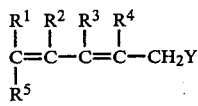

is reacted with a compound of the formula

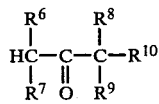

wherein $R^1$ through $R^{10}$ are as defined above and Y represents halogen, in the presence of a base to form a ketone of formula I, said ketone being a compound of this invention which may, if desired, (a) be reduced to give a secondary alcohol of formula I, or (b) be converted into a tertiary alcohol of formula I by reaction with a compound of the formula $R^{11}$Mg Y, or (c) be converted into an oxime of formula I by reaction with hydroxylamine.

The reaction of a compound of formula II with a compound of formula III can be carried out according to methods known per se.

The chloride, bromide or iodide can be used as the halide of formula II. The chloride is preferred.

The reaction between compounds II and III is preferably carried out in the presence of a strong inorganic base such as, for example, an alkali metal hydroxide (e.g. potassium hydroxide), an alkaline earth hydroxide (e.g. calcium hydroxide), an alkali metal amide (e.g. sodium amide) or an alkali metal hydroxide (e.g. sodium hydride) or, however, also an organic base such as, for example, potassium tert. butoxide.

This reaction can be carried out in the presence or absence of a solvent. Especially suitable solvents are aprotic or slightly polar solvents; for example, dimethoxymethane, dimethoxyethane, diethyl ether or tetrahydrofuran or, however, also toluene or benzene.

This reaction between II and III is conveniently carried out at a temperature between approximately $-20°$ and $+50°$ C., preferably between $-10°$ and $+20°$ C. Lower temperatures are industrially unpractical and higher temperatures could easily lead to the formation of undesired polymeric by-products.

The reaction between II and III can also be carried out in the presence of a phase transfer agent, such as tricaprilyl methyl ammonium chloride (e.g. Aliquat 336 by Henkel).

The reaction of the initially obtained ketone of formula I with a compound of the formula R''Mg Y is conveniently carried out according to methods which are known per se for the Grignard reaction; see, for example, Organikum, Organisch-chemisches Grundpraktikum, collective authors; 7th Edition; VEB Deutscher Verlag der Wissenschaften; Berlin 1967, 486 seq.

Thus, the reaction is conveniently carried out in diethyl ether as the solvent and at temperatures between 0° C. and the boiling point of the ether.

The usual halides come into consideration as the halide, but the bromide is preferred.

An initially obtained ketone of formula I can be reduced to a secondary alcohol, preferably using reducing agents such as sodium borohydride, lithium aluminium hydride, triisopropylaluminate etc. (L. F. Fieser and M. Fieser, Reagents for Organic Synthesis, John Wiley & Sons (1967), 581, 582, 584, 1049 and Organikum, loc. cit., pages 475-476).

Solvents which especially come into consideration are ethanol or water when sodium borohydride is used, diethyl ether when lithium aluminum hydride is used and isopropanol when triisopropylaluminate is used.

On the other hand, an initially obtained ketone of formula I can be converted into the corresponding oxime by reaction with hydroxylamine. The reaction is conveniently carried out according to methods known per se; see, for example, Organikum, Organisch-Chemisches Grundpraktikum, collective authors; 7th Edition; VEB Deutscher Verlag der Wissenschaften; Berlin 1967, 375. The hydroxylamine is conveniently used in the form of a salt (e.g. the hydrochloride or sulphate) and is reacted with the ketone of formula I in a pyridine-containing alkaline solution or in an aqueous-alkaline solution. In this case, the reaction is preferably carried out at the reflux temperature of the reaction mixture.

The compounds of formula I have particular organoleptic properties, on the basis of which they are excellently suited as odorant substances.

The invention is also concerned with the use of the compounds of formula I as odorant substances.

The compounds of formula I have an odour which is generally reminiscent of notes of bergamot oil, lavender, sage and lemon peel. On the basis of their natural olfactory notes and their tenacity (long-lasting effect, especially with regard to freshness) the compounds of formula I are especially suitable for the modification of, for example, ($\alpha$) known flowery compositions in which, for example, the citrus notes are to be emphasised (e.g. for cologne types and the like, essences ("extraits")), ($\beta$) known fruity compositions, for example, of the currant type (essence types, composition of the feminine as well as the masculine direction), ($\gamma$) known compositions having green notes in which, in particular, a desired natural effect is produced, and finally of ($\delta$) known compositions of the agrestic type (namely compositions having "rustic notes").

Especially interesting compounds are:

2,4,4-Trimethyl-6,8-nonadien-3-one:

This compound has a very natural lavender note. Further, the odour is reminiscent of blackcurrants of, cut stinging nettles and of basil. This compound produces surprising effects in compositions, namely a natural harmonic rounding-off on the one hand and an accentuation of a pleasant, flowery note on the other hand.

2,2-Dimethyl-6,8-nonadien-3-ol:

The odour of this compound is fruity (especially citrus), earthy and flowery in the direction of sage flowers. The aldehydic olfactory character of this alcohol is surprising. In compositions the citrus-sage complex gives an original note which is especially valuable in mens perfumes.

2,4,4,7-Tetramethyl-6,8-nonadien-3-one:

The odour of this compound is fresh, natural and reminiscent of blackcurrants and of bergamot oil.

3-Ethyl-4,7-dimethyl-6,8-nonadien-3-ol:

This tertiary alcohol is distinguished especially by its diffusion. The olfactory note is lavender-like and is very natural. Surprising effects are produced in compositions in that this alcohol confers thereto more volume and the compositions are rounded-off in a harmonic manner.

2,3,4,4,7-Pentamethyl-6,8-nonadien-3-ol:

The olfactory note is fruity, somewhat earthy, reminiscent of grapefruit and with a mushroom and a woody bottom note.

2,4,4,7-Tetramethyl-6,8-nonadien-3-one oxime:

This compound has a very natural note after blackcurrants, with an extraordinary tenacity.

Other preferred compounds of formula I are:
2,2,7-Trimethyl-6,8-nonadien-3-one,
2,2,7-trimethyl-6,8-nonadien-3-ol,
2,2,3,7-tetramethyl-6,8-nonadien-3-ol,
3,6-dimethyl-5,7-octadien-2-ol,
5-isopropyl-2,9-dimethyl-7,9-decadien-4-one,
2,4,4,7,8-pentamethyl-6,8-nonadien-3-one,
2,4,4,8-tetramethyl-6,8-nonadien-3-ol,
3,3,6-trimethyl-5,7-octadien-2-one,
5-ethyl-8-methyl-7,9-decadien-4-one,
3,3,6-trimethyl-5,7-octadien-2-one oxime and
5-ethyl-8-methyl-7,9-decadien-4-one oxime.

The compounds of formula I combine with numerous known natural or synthetic ingredients of odorant compositions, whereby the range of the natural ingredients can embrace not only readily-volatile but also semi-volatile and difficulty-volatile substances and the range of synthetic ingredients can embrace representatives from almost all classes of substances, as will be evident from the following compilation:

Natural products such as tree moss absolute, basil oil, bergamot oil, acetylated cedarwood oil (e.g. Vertofix TM, IFF or Cedartone TM, Givaudan), oak moss, camomile oil, galbanum oil, geranium oil, jasmine absolute and its substitute, lavender oil, lavandin oil, mastix absolute, coriander oil, neroli oil, patchouli oil, petit-grain oil Paraguay, elemi oil, sandalwood oil, vetiver oil, ylang-ylang oil, lemon oil, wormwood oil, angelica seed oil, rosemary oil, mandarine oil, hyssop oil.

Alcohols such as linalool, citronellol, geraniol, natural rhodinol, $\alpha$-terpineol, phenylethyl alcohol, phenylpropyl alcohol, cinnamic alcohol, 3-methyl-5-(2',2',3'-trimethyl-cyclopent-3'-en-1'-yl)-pentan-2-ol (Sandalore ®, Givaudan), dimethylbenzyl carbinol, terpineol, menthol, 2,2,8-trimethyl-7-nonen-3-ol.

Aldehydes such as 3,5-dimethyl-cyclohex-3-ene-carboxaldehyde, decanal, methylnonylacetaldehyde, hydroxycitronellal, $\alpha$-hexylcinnamaldehyde, cyclamen aldehyde, p-tert.butyl-$\alpha$-methyl-dihydro-cinnamaldehyde (e.g. Lilial ® Givaudan), citral, $\alpha$-amylcinnamaldehyde, n-undecen-10-al, n-dodecanal.

Ketones such as $\alpha$-ionone, acetylcedrene, p-methylacetophenone, methylionone, allylionone, p-hydroxybenzylacetone.

Esters such as cedryl acetate, cis-3-hexenyl acetate, cis-3-hexenyl benzoate, ethyl acetoacetate, linalyl acetate, geranyl acetate, terpenyl acetate, phenylethyl acetate, styrallyl acetate, p-tert.butylcyclohexyl acetate, 4-[4-methyl-3-pentenyl]-cyclohex-3-en-1-yl-carbinyl acetate (e.g. Myraldylacetat TM, Givaudan), cinnamyl formate, benzyl acetate, benzyl salicylate, amyl salicylate, isobutyl salicylate, hexyl salicylate, methyl dihydrojasmonate, 3-ethyl-1,1-dimethyl-cyclohex-3-ene-2-carboxylic acid ethyl ester (Givescone TM, Givaudan), linalyl anthranilate, 3-ethyl-1,1,4-trimethyl-cyclohex-3-ene-2-carboxylic acid ethyl ester (Myrascone TM, Givaudan).

Lactones such as $\gamma$-nonalactone, $\gamma$-decalactone, $\gamma$-undecalactone, $\gamma$-dodecalactone, coumarin.

Various additional ingredients often used in perfumery such as musk compounds (musk ketone, 12-oxahexadecanolide (e.g. Musk 174 TM, Naarden), 1,1-dimethyl-4-acetyl-6-tert.butylindane), indole, p-methane-8-thiol-3-one, eugenol, acetaldehyde propylphenyl-ethyl acetal, methyl 1-methyl-cyclododecyl ether (e.g. Madrox TM, Givaudan), phenylacetaldehyde dimethyl acetal (Viridine TM), cyclocitrylidene-acetonitrile, 8$\alpha$,12-oxido-13,14,15,16-tetranorlabdan (Fixateur 404 TM).

The compounds of formula I can be used within wide limits which, for example, can extend in compositions from 0.1% in the case of detergents to 50% in the case of alcoholic solutions. It will be appreciated that these values are not limiting values, since the experienced perfumer can also produce effects with still lower concentrations or can synthesise novel complexes with still higher concentrations. The preferred concentrations vary between 0.5% and 25%. The compositions produced with compounds of formula I can be used for all types of perfumed consumer goods (Eau de Cologne, eau de toilette, essences("extraits"), lotions, creams, shampoos, soaps, salves, powders, deodorants, detergents, tobacco etc).

The compounds of formula I can accordingly be used in the production of odorant compositions and, as will be evident from the foregoing compilation, using a wide range of known odorant substances. In the production of such compositions the known odorant substances specified above can be used according to methods known to the perfumer such as, for example, according to W. A. Poucher, Perfumes, Cosmetics and Soaps 2, 7th Edition, Chapman and Hall, London, 1974.

The following Examples illustrate the present invention:

EXAMPLE 1

2,4,4-Trimethyl-6,8-nonadien-3-one 60 g of powdered potassium hydroxide and 180 ml of dry toluene are placed in a 1 liter round flask which is provided with a stirrer, thermometer, condenser and dropping funnel. The mixture is cooled to $-10°$ C. and a mixture of 30 g of 1-chloro-2,4-pentadiene and 33 g of diisopropyl ketone is allowed to drop in within 35 minutes while stirring. During the addition the temperature is held below 0° C., then it is allowed to rise to 20° C. and the reaction mixture is stirred for a further 7 hours. The mixture is left to stand for 12 hours and then the flask content is poured on to 200 g of crushed ice. The layers formed are separated and the organic layer is washed neutral with water. The solvent is evaporated off and there remain behind 40 g of crude product which are subjected to a fractional distillation.

Boiling point of the pure 2,4,4-trimethyl-6,8-nonadien-3-one: 54° C./0.75 mm Hg; $n_D^{20}=1.4711$; $d_4^{20}=0.8623$. Odour: lavender-like, natural, reminiscent of cut stinging nettles and of blackcurrants.

EXAMPLE 2

2,2-Dimethyl-6,8-nonadien-3-one

A mixture of 34 g of 1-chloro-2,4-pentadiene and 34.7 g of 3,3-dimethyl-butan-2-one (pinacolin) is added dropwise within 80 minutes while stirring at a temperature of 40° C. to 45° C. to 76 g of powdered potassium hydroxide in 230 ml of dry toluene. The mixture is now cooled to room temperature and the flask content is poured on to 200 g of crushed ice. The layers formed are separated and the organic layer is washed neutral. The solvent is distilled off and there are obtained 56 g of crude product which are subjected to a fractional distillation.

Boiling point of the pure 2,2-dimethyl-6,8-nonadien-3-one: 57° C./1.2 mm Hg; $n_D^{20}=1.4700$; $d_4^{20}=0.8618$. Odour: rose-like, somewhat camphorous, reminiscent of phenylethyl isobutyrate.

EXAMPLE 3

2,2-Dimethyl-6,8-nonadien-3-ol 6.8 g of lithium aluminium hydride and 150 ml of dry ether are placed in a 1 liter round flask which is provided with a stirrer, thermometer, condenser and dropping funnel. To the resulting suspension is added dropwise within 2 hours while stirring at a temperature of 0° C. a solution of 30 g of 2,2-dimethyl-6,8-nonadien-3-one in 300 ml of dry ether. After the addition, the mixture is held at the reflux temperature for 4 hours. After cooling, the excess lithium aluminium hydride is decomposed with 30 ml of ethyl acetate. The flask content is poured into ice-cold 10% sulphuric acid, the layers formed are separated and the organic layer is washed successively with water, 8% sodium hydrogen carbonate solution and again with water until neutral. After drying over sodium sulphate, the ether is evaporated off and the residue (35 g) is distilled.

Boiling point of the pure 2,2-dimethyl-6,8-nonadien-3-ol: 78° C./2.5 mm Hg; $n_D^{20}=1.4809$; $d_4^{20}=0.8654$. Odour: fruity, after lavender, somewhat mushroom-like.

EXAMPLE 4

2,2-Dimethyl-6,8-decadien-3-one

According to the procedure described in Example 2, from 19.4 g of 1-chloro-2,4-hexadiene and 17.4 g of 3,3-dimethyl-butan-2-one there are obtained 30 g of crude 2,2-dimethyl-6,8-decadien-3-one which are subjected to a fractional distillation.

Boiling point of the pure product: 49° C./0.1 mm Hg; $n_D^{20}=1.4755$; $d_4^{20}=0.8613$. Odour: Fruity, after pears, reminiscent of geranyl formate, rose-like.

EXAMPLE 5

2,2-Dimethyl-6,8-decadien-3-ol

According to the procedure described in Example 3, by reducing 16.2 g of 2,2-dimethyl-6,8-decadien-3-one with 3.4 g of lithium aluminium hydride in 250 ml of dry ether there are obtained 17 g of crude product which gave 7.8 g of pure 2,2-dimethyl-6,8-decadien-3-ol by fractional distillation.

Boiling point: 62° C./0.2 mm Hg; $n_D^{20}=1.4861$; $d_4^{20}=0.8703$; odour: lavender-like, mushroom-like, reminiscent of unripe mandarins.

EXAMPLE 6

2,4,4,8-Tetramethyl-6,8-nonadien-3-one

According to the procedures described in Example 1, from 58 g of 1-chloro-4-methyl-2,4-pentadiene and 59 g of diisopropyl ketone there are obtained 57 g of crude 2,4,4,8-tetramethyl-6,8-nonadien-3-one which are subjected to a fractional distillation.

Boiling point of the pure product: 53° C./0.25 mm Hg; $n_D^{20}=1.4770$; $d_4^{20}=0.8701$; odour: lavender-like, bergamotte, resembling linalyl acetate.

EXAMPLE 7

2,4,4,7-Tetramethyl-6,8-nonadien-3-one 264 g of powdered potassium hydroxide and 800 ml of dry toluene are placed in a 2 liter round flask which is provided with a stirrer, thermometer, condenser and dropping funnel. The mixture is cooled to $-10°$ C. and a mixture of 153.5 g of 1-chloro-3-methyl-2,4-pentadiene and 151 g of diisopropyl ketone are added dropwise thereto while stirring during 2 hours, the temperature being held below 0° C. by external cooling. After the addition, the mixture is stirred at room temperature for a further 6 hours. The mixture is left to stand for 12 hours and then the flask content is poured on to 500 g of crushed ice. The layers formed are separated and the organic layer is washed neutral with water. The solvent is evaporated off and there remain behind 160 g of crude product which are subjected to a fractional distillation.

Boiling point of the pure 2,4,4,7-tetramethyl-6,8-nonadien-3-one: 64° C./0.3 mm Hg; $n_D^{20}=1.4790$; $d_4^{20}=0.8733$; odour: fruity, after bergamotte, ocimene, very natural.

EXAMPLE 8

2,2,7-Trimethyl-6,8-nonadien-3-one

According to the procedure described in Example 7, from 116 g of 1-chloro-3-methyl-2,4-pentadiene and 100 g of 3,3-dimethyl-butan-2-one in the presence of 200 g of powdered potassium hydroxide in 600 ml of toluene there are obtained 141 g of crude 2,2,7-trimethyl-6,8-nonadien-3-one which are subjected to a fractional distillation.

Boiling point of the pure product: 50° C./0.1 mm Hg; $n_D^{20} = 1.4763$; $d_4^{20} = 0.8699$; Odour: lavender-like, ocimene, but much better adhesion than ocimen.

EXAMPLE 9

4,7-Dimethyl-6,8-nonadien-3-one

According to the procedure described in Example 1, from 58 g of 1-chloro-3-methyl-2,4-pentadiene and 43 g of pentan-3-one (diethyl ketone) in the presence of 50 g of powdered potassium hydroxide in 200 ml of dry pentane there are obtained 51 g of crude 4,7-dimethyl-6,8-nonadien-3-one which are subjected to a fractional distillation.

Boiling point of the pure product: 86° C./6 mm Hg; $n_D^{20} = 1.4788$; $d_4^{20} = 0.8782$; odour: lavender-like, fruity, allylic, reminiscent of grapefruit.

EXAMPLE 10

3-Ethyl-4,7-dimethyl-6,8-nonadien-3-ol

Ethyl magnesium bromide is prepared from 9.4 g (0.39 gram atom) of magnesium and 44.6 g (0.41 mol) of ethyl bromide in 210 ml of dry ether in a 1 liter round flask which is provided with a thermometer, stirrer, condenser and dropping funnel. Thereto there is added a solution of 64.5 g (0.39 mol) of 4,7-dimethyl-6,8-nonadien-3-one in 200 ml of dry ether. After completion of the addition, the mixture is held at reflux temperature for 3 hours and thereafter cooled in an ice-bath. The magnesium complex formed is decomposed by adding a solution of 30 g of ammonium chloride in 300 ml of water. The organic phase is separated and the aqueous layer is extracted three times with 50 ml of ether each time. The combined organic phases are washed neutral with 5% tartaric acid, with water, with 8% sodium bicarbonate solution and thereupon with water. The ether is evaporated off and the crude product (72 g) is distilled.

Boiling point of the pure 3-ethyl-4,7-dimethyl-6,8-nonadien-3-ol: 65° C./0.2 mm Hg; $n_D^{20} = 1.4947$; $d_4^{20} = 0.8935$; odour: very natural after lavender, clinging and diffuse.

EXAMPLE 11

5-Isopropyl-2,9-dimethyl-7,9-decadien-4-one

According to the procedure described in Example 1, from 1-chloro-4-methyl-2,4-pentadiene and 2,6-dimethyl-heptan-4-one there is obtained the above ketone; b.p. = 72° C./0.3 mm Hg; $n_D^{20} = 1.4728$. Odour: linalool-like with a musk note, very natural.

EXAMPLE 12

2,4,4,7,8-Penntamethyl-6,8-nonadien-3-one

According to the procedure described in Example 1, from 1-chloro-3,4-dimethyl-2,4-pentadiene and diisopropyl ketone there is obtained the above ketone; b.p. = 74° C./0.22 mm Hg; $n_D^{20} = 1.4795$. Odour: lavender-like, amber-like, mushroom-like, somewhat woody.

EXAMPLE 13

2,2,7-Trimethyl-6,8-nonadien-3-ol 41.8 g of 2,2,7-trimethyl-6,8-nonadien-3-one, 20 ml of water and 54 ml of ethanol are placed in a 1 liter round flask which is provided with a stirrer and thermometer. 6.1 g of sodium borohydride are added portionwise to this mixture while stirring, the temperature being held at 25° C. by external cooling. After the addition, the mixture is stirred at 25° C. for a further 3 hours. The mixture is neutralised with a tartaric acid solution while cooling and then acidified slightly. The mixture is taken up in ether, washed with water until neutral and the ethereal solution is dried over sodium sulphate. The ether is evaporated off and the residue (41.4 g) is distilled.

Boiling point of the pure 2,2,7-trimethyl-6,8-nonadien-3-ol: 59°-60° C./0.2 mm Hg; $n_D^{20} = 1.4863$. Odour: fruity, after lavender flowers, very natural.

EXAMPLE 14

2,4,4,8-Tetramethyl-6,8-nonadien-3-ol

According to the procedure described in Example 3, by reducing 2,4,4,8-tetramethyl-6,8-nonadien-3-one with lithium aluminium hydride in diethyl ether there is obtained the corresponding secondary alcohol having the boiling point 89° C./0.8 mm Hg; $n_D^{20} = 1.4910$. Odour: lavender-like, somewhat balsamic.

EXAMPLE 15

2,2,3,7-Tetramethyl-6,8-nonadien-3-ol

According to the procedure described in Example 10, from 2,2,3,7-tetramethyl-6,8-nonadien-3-one and methylmagnesium iodide there is obtained the above alcohol having the boiling point 62° C./0.05 mm Hg; $n_D^{20} = 1.4910$. Odour: reminiscent of lavender seeds, very natural and with good adhesion.

EXAMPLE 16

According to the procedure described in Example 10, from 58.3 g of 2,4,4,7-tetramethyl-6,8-nonadien-3-one and methylmagnesium iodide (ex 7.2 g of magnesium) there are obtained 57.9 g of crude 2,3,4,4,7-pentamentyl-6,8-nonadien-3-ol which are subjected to a fraction distillation.

Boiling point of the pure product: 79° C./0.3 mm Hg; $n_D^{20} = 1.4983$; $d_4^{20} = 0.9011$. Odour: fruity, reminiscent of grapefruit, somewhat earthy, powdery, woody.

EXAMPLE 17

A solution of 127 g of 2,4,4,7-tetramethyl-6,8-nonadien-3-one and 127 g of hydroxylamine hydrochloride in 127 ml of pyridine and 1.27 liters of ethanol is held at reflux temperature for 2 hours in a round flask provided with a stirrer, thermometer and condenser. Thereupon, the majority of the ethanol is distilled off. After cooling, the mixture is poured into ice/water and taken up in ether. The ether solution is washed firstly with water and then with 5% hydrochloric acid (elimination of the excess pyridine) and subsequently again with water until neutral. After evaporation of the ether, there are obtained 109 g of crude product which still contain 86 g of unreacted ketone. The ketone is distilled off. The residue consists of the oxime as an isomer mixture and can be used in perfumery in the form of a 10% alcoholic solution.

A portion of the residue is separated by column chromatography: 17.8 g of residue are dissolved in toluene and chromatographed on 500 g of silica gel. There are obtained 12 fractions, whereby fractions 2 and 3 on the one hand and 10 and 11 are obtained crystalline. After recrystallisation of fractions 2 and 3 from methanol and water, there is obtained one of the oxime isomers having a melting point of 68°–70° C.

EXAMPLE 18

According to the procedure described in Example 1, from 58.1 g of 1-chloro-2,4-pentadiene and 45.2 g of isopropyl methyl ketone in the presence of 100 g of powdered potassium hydroxide in 300 ml of toluene there are obtained 49.9 g of crude 3,3,6-trimethyl-5,7-octadien-2-one which are subjected to a fraction distillation.

Boiling point of the pure product: 83° C./6 mm Hg; $n_D^{20} = 1.4815$; $d_4^{20} = 0.8913$. Odour: ocimene-like, reminiscent of cooked rhubarb.

EXAMPLE 19

According to the procedure described in Example 1, from 116.6 g of 1-chloro-2,4-pentadiene and 114.2 g of dipropyl ketone (heptan-4-one) in the presence of 200 g of powdered potassium hydroxide in 600 ml of toluene there are obtained 91.9 g of crude 5-ethyl-8-methyl-7,9-decadien-4-one which are subjected to a fractional distillation.

Boiling point of the pure product: 61° C./0.2 mm Hg; $n_D^{20} = 1.4770$; $d_4^{20} = 0.8713$. Odour: fruity, cooked pears, plums.

EXAMPLE 20

According to the procedure described in Example 17, from 33.2 g of 3,3,6-trimethyl-5,7-octadien-2-one there are obtained 33.9 g of crude oxime which are subjected to a fractional distillation.

Boiling point of the pure product: 73° C./0.15 mm Hg; $n_D^{20} = 1.5072$; $d_4^{20} = 0.9339$. Odour: green, natural, reminiscent of grapefruit and celery.

EXAMPLE 21

26.3 g of hydroxylamine sulphate are dissolved in 55 ml of water in a 500 ml round flask provided with a stirrer, thermometer, condenser and dropping funnel. 52 g of 33% sodium hydroxide are added thereto and the temperature is held at 25° C. by cooling during the addition. Then, there is slowly added dropwise thereto at room temperature a solution of 61 g of 5-ethyl-8-methyl-7,9-decadien-4-one in 120 ml of ethanol. Thereupon, the mixture is held at reflux temperature for 4 hours. After cooling, the mixture is poured into ice/water, taken-up in ether and washed neutral. The solvent is distilled off and there are obtained 64.3 g of crude oxime which are fractionally distilled.

Boiling point of the pure product: 95° C./0.2 mm Hg; $n_D^{20} = 1.4997$; $d_4^{20} = 0.9141$. Odour: after celery stalks, very natural, somewhat after grapefruit, good adhesion.

EXAMPLE 22

50 parts by weight of 2,4,4-trimethyl-6,8-nonadien-3-one (Example 1) are added to a perfumery base in the direction of linden flower containing

|  | Parts by weight |
|---|---|
| Hydroxycitronellal | 150 |
| Linalool | 150 |
| α-Ionone | 100 |
| p-tert. Butyl-α-methylhydrocinnamaldehyde (LILIAL ®) | 100 |
| Phenylethyl alcohol | 100 |
| Hexyl salicylate | 50 |
| Linalyl anthranilate | 50 |
| Galbanum (synthetic) (10% DPG) (dipropyleneglycol) | 20 |
| Roman camomile oil (1% DPG) | 10 |
| Eugenol | 5 |
| Coumarin | 5 |
| DPG | 210 |
|  | 950 |

In this manner the pleasant flowery, sweet note, which confers to the composition a rounded-off, powdery character, is underlined in a welcome manner. On the basis of its tenacity, the novel base obtained is especially suitable for the perfuming of soaps.

EXAMPLE 23

50 parts by weight of 2,2-dimethyl-6,8-nonadien-3-ol (Example 3) are added to a perfumery base in the direction of cyclamen containing

|  | Parts by weight |
|---|---|
| 2-Ethyl-3,6,6-trimethyl-2-cyclohexene-carboxylic acid ethyl ester | 150 |
| Cyclamenaldehyde [3-[p-isopropylphenyl-2-methyl]-propionaldehyde] | 100 |
| Linalyl acetate | 80 |
| Geraniol | 80 |
| Benzyl acetate | 70 |
| Hydroxycitronellal | 50 |
| αHexylcinnamaldehyde | 50 |
| p-tert-Butyl-α-methylhydrocinnamaldehyde (LILIAL ®) | 50 |
| Linalool | 50 |
| $C_{12}$—aldehyde (10% DPG) | 20 |
| 2-Ethyl-6,6-dimethyl-2-cyclohexene-carboxylic acid ethyl ester | 20 |
| DPG | 230 |
|  | 950 |

The somewhat raw benzyl acetate note predominates in the original base; this becomes more flowery, softer and warmer after the addition. The novel composition has substantially more volume and more diffusion.

EXAMPLE 24

50 parts by weight of 2,2-dimethyl-6,8-nonadien-3-ol (Example 3) are added to a perfumery base in the direction of Fougere containing

|  | Parts by weight |
|---|---|
| Methyl 1-methyl-cyclododecyl ether | 150 |
| 2,2,8-Trimethyl-7-nonen-3-ol | 150 |
| Bergamot oil | 80 |
| 12-Oxahexadecanolide (Musk 174 ™) | 70 |
| Hydroxycitronellal | 70 |
| Coriander oil | 50 |
| Patchouli oil | 50 |
| Tree moss (50% DPG) | 30 |
| Galbanum oil | 30 |
| Rhodinol | 30 |
| Isomethyl-α-ionone (ISORALDEIN ®) | 30 |
| Petitgrain oil | 20 |
| Allylionone | 20 |

-continued

| | Parts by weight |
|---|---|
| Elemi oil | 15 |
| Angelica seed oil | 10 |
| Geranium oil (synthetic) | 10 |
| DPG | 85 |
| | 900 |

Following the addition the composition has a citrus note in the direction of sage and becomes more powerful and fresher. The addition of the novel compound underlines in the composition the citrus-sage complex, which confers to the composition an extraordinarily original note. The novel composition is very well suited for modern mens lines.

EXAMPLE 25

50 parts by weight of 2,2-dimethyl-6,8-decadien-3-ol (Example 5) are added to the perfumery base of Example 16 (direction of linden flower). An aldehydic character is thereby conferred to the composition, which is very well suited for the perfuming of cosmetic preparations.

EXAMPLE 26

150 parts by weight of 2,4,4,8-tetramethyl-6,8-nonadien-3-one (Example 6) are added to a composition in the direction of cologne containing

| | Parts by weight |
|---|---|
| Lemon oil | 300 |
| Bergamot oil | 200 |
| Neroli oil | 70 |
| Rosemary oil | 70 |
| Petitgrain oil | 50 |
| 4-t-Butyl-3,5-dinitro-2,6-dimethylacetophenone (Musk ketone) | 20 |
| Mandarin oil | 15 |
| Hydroxycitronellal | 10 |
| Eugenol | 10 |
| Linalyl anthranilate | 5 |
| DPG | 100 |
| | 850 |

After this addition, the composition becomes substantially "more powerful" with the citrus note being surprisingly altered in the direction of grapefruit. Moreover, there now appears a woody-green note which provides the composition with a vetiver character and therewith it can appear much more precious.

EXAMPLE 27

Perfumery complex in the direction of sage containing

| | Parts by weight |
|---|---|
| 2,2,8-Trimethyl-7-nonen-3-ol | 200 |
| Methyl dihydrojasmonate | 100 |
| Bergamot oil | 100 |
| Methyl 1-methylcyclododecyl ether | 100 |
| Hyssop oil | 80 |
| Allylionone | 30 |
| p-Methane-8-thiol-3-one (1°/$_{oo}$) | 5 |
| 8a,12-oxido-13,14,15,16-tetranorlabdane (Fixateur 404 TM) | 5 |
| DPG | 280 |
| | 900 |

The base is reminiscent of sage plant. By the addition of 100 parts by weight of 2,4,4,7-tetramethyl-6,8-nonadien-3-one (Example 7) there results a novel complex which is reminiscent of sage flowers and is much fresher and more powerful than the original base.

EXAMPLE 28

The woody pleasant note of the following "Chypre" composition in the direction of vetiver is clearly intensified by the addition of 100 parts by weight of 3-ethyl-4,7-dimethyl-6,8-nonadien-3-ol (Example 10).

| | Parts by weight |
|---|---|
| 2-Ethyl-3,6,6-trimethyl-2-cyclohexene-carboxylic acid ethyl ester | 100 |
| Isomethyl-α-ionone (ISORALDEIN ®) | 100 |
| Geraniol | 60 |
| Methyl dihydrojasmonate | 60 |
| Bergamot oil | 50 |
| 4-t-Butyl-3,5-dinitro-2,6-dimethyacetophenone (Musk ketone) | 35 |
| 2,2,8-Trimethyl-7-nonen-3-ol | 30 |
| Linalool | 30 |
| Benzyl acetate | 20 |
| Methyl 1-methyl-cyclododecyl ether | 20 |
| Patchouli oil | 15 |
| 3-Methyl-5-(2,2,3,-trimethylcyclopent-3-en-1-yl)pentan-2-ol (SANDALORE ®) | 10 |
| cyclocitrylidene-acetonitrile | 5 |
| Styrallyl acetate | 5 |
| $C_{11}$—aldehyde (10% DPG) | 5 |
| Undecalactone | 3 |
| p-Hydroxybenzylacetone | 2 |
| DPG | 350 |
| | 900 |

There is obtained an effect which fixes the active substances and this enriches the base in an extraordinary manner. The base can be used without further ado as a finished perfume extract.

EXAMPLE 29

Perfumery base in the direction of wood

| | Parts by weight |
|---|---|
| Methyl 1-methylcyclododecyl ether | 150 |
| Vetivenyl acetate | 100 |
| 3-Isocamphyl-(5)-cyclohexanol + isomers (SANDELA ®, Givaudan) | 100 |
| Linalool | 100 |
| Patchouli oil | 50 |
| Irone | 50 |
| Linalyl acetate | 50 |
| Citronellol | 50 |
| Benzyl acetate | 30 |
| Tree moss (colourless, absolute) | 30 |
| α-Amylcinnamaldehyde | 20 |
| Methylnonylacetaldehyde (10% DPG) | 20 |
| Eugenol | 20 |
| $C_{11}$—aldehyde (10% DPG) | 10 |
| Ciste oil (French) | 10 |
| 3-Methyl-5-(2,2,3-trimethylcyclopent-3-en-1-yl)pentan-2-ol (SANDALORE ®) | 10 |
| | 800 |

If 200 parts 2,3,4,4,7-pentamethyl-6,8-nonadien-3-ol are added to this woody perfumery base, then it is rounded-off in an extremely pleasant manner. The previously far too dominating vetivenyl acetate note is supressed in favour of a pleasant fresh-green note which still predominates even after 24 hours.

EXAMPLE 30

Perfumery cologne

| | Parts by weight |
|---|---|
| Bergamot oil | 80 |
| 2-Ethyl-3,6,6,-trimethyl-2-cyclohexen-1-yl-carboxylic acid ethyl ester | 80 |
| 1,3,4,6,7,8-Hexahydro-4-6,6,7,8,8-hexa-methyl-cyclopenta-γ-2-benzopyran (Galaxolide TM) | 60 |
| Hydroxycitronellal | 60 |
| Methyl-1-methylcyclododecyl ether | 60 |
| Bornyl acetate | 40 |
| Musk ketone | 40 |
| 3-Ethyl-1,1,-dimethyl-cyclohex-3-ene-2-carboxylic acid ester (Givescone TM) | 20 |
| Petitgrain oil | 20 |
| 3-Methyl-5-(2,2,3-trimethyl-cyclopent-3-en-1-yl)pentan-2-ol (SANDALORE ®, Givaudan) | 30 |
| p-Methane-8-thiol-3-one | 5 |
| Tree moss (absolute) | 5 |
| Dipropyleneglycol | 450 |
| | 950 |

This is a classical cologne base which is enormously enriched organoleptically by the addition of 100 parts of 2,3,4,4,7-pentamethyl-6,8-nonadien-2-ol. The cologne is completely altered; by an underlining of the linaloolcassis note it becomes very much more powerful, fresher and fuller in character.

If the same amount of a 10% alcoholic solution of the oxime of 2,4,4,7-tetramethyl-6,8-nonadien-3-one (crude product of Example 17) is added thereto, then the effect is similar.

Furthermore, in this case, an amazingly natural coriander character is established.

EXAMPLE 31

Flowery complex

| | Parts by weight |
|---|---|
| Hydroxycitronellal | 700 |
| 2,4,4,7-Tetramethyl-6,8-nonadien-3-one | 60 |
| Hexyl salicylate | 40 |
| | 800 |

By the addition of 200 parts of 5-ethyl-8-methyl-7,9-decadien-4-one oxime this flowery complex is modified in the direction of linden flower. The previously green-flowery complex also now exhibits in addition, entirely suprisingly, a powdery note.

If, however, the same amount of a 10% alcoholic solution of the oxime of 2,4,4,7-tetramethyl-6,8-nonadien-3-one (crude product of Example 17) is added to this complex, it is modified very effectively in a spicy direction. The composition is especially suitable for soaps and for detergent bases.

EXAMPLE 32

Animal base

| | Parts by weight |
|---|---|
| 3-Isocamphyl-(5)-cyclohexanol + isomers (SANDELA ®, Givaudan) | 100 |
| Methyl 1-methylcyclododecyl ether | 100 |
| Acetylcedrene | 100 |
| Patchouli oil | 50 |

-continued

| | Parts by weight |
|---|---|
| Benzyl salicylate | 40 |
| Linalyl acetate | 40 |
| Myrrh oil | 30 |
| Benzoin resinoid (Siam) | 30 |
| Ethylene brassylate | 30 |
| Castoreum (synthetic) | 30 |
| ω-Undecenal | 20 |
| Dodecanal | 20 |
| β-Ionone | 20 |
| p-Cresyl-phenylacetate | 5 |
| Indole | 5 |
| DPG up to | 1000 |

If 100 parts of 5-ethyl-8-methyl-7,9-decadien-4-one oxime (Example 21) are added to this base having an animal character, then it is underlined extremely effectively, a fact which is surprising having regard to the odour of the oxime itself. The base is now much warmer and, moreover, exhibits more volume.

EXAMPLE 33

Spicy base

| | Parts by weight |
|---|---|
| Benzyl acetate | 100 |
| Hydroxycitronellal | 100 |
| Phenylethyl alcohol | 100 |
| Amyl salicylate | 100 |
| Patchouli oil | 80 |
| Ylang oil | 50 |
| Eugenol | 50 |
| Linalyl acetate | 60 |
| Musk ketone | 50 |
| Cedryl acetate | 30 |
| Epoxycedrene | 30 |
| Acetyl-cedrene | 30 |
| Coumarin | 30 |
| Spearmint oil | 15 |
| Sage oil | 15 |
| Lemon oil | 5 |
| DPG up to | 1000 |

By the addition of 50 parts of a 10% solution of the oximes of 2,4,4,7-tetramethyl-6,8-nonadien-3-one (Example 17) there is introduced into this base, which originally has a heavy-sweet direction, a minty-spicy note; The total note now stands out in an impressive manner from the note of the original base. The complex spearmint-lemon-sage is emphasized.

The addition of 100 parts of 3,3,6-trimethyl-5,7-octadien-2-one oxime (Example 20) also confers more life and freshness to the base. The lavender-like note of the oxime itself combines very advantageously with the spicy-flowery element of the base to give a fougère-like, complex effect.

I claim:

1. A compound of the formula

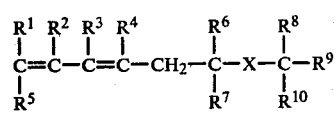

wherein:
(i) X stands for

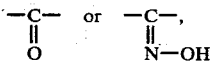

(ii) $R^1$ through $R^{10}$ are alike or different and are selected from the group consisting of hydrogen, methyl, ethyl, n-propyl and isopropyl except that when both $R^6$ and $R^7$ are hydrogen, none of the groups $R^8$, $R^9$, or $R^{10}$ is hydrogen, and (iii) the total number of carbon atoms in the molecule does not exceed fifteen.

2. A compound according to claim 1 wherein X stands for

3. A compound according to claim 1 identified as 2,2,4-trimethyl-6,8-nonadien-3-one.

4. A compound according to claim 1 identified as 2,2,7-trimethyl-6,8-nonadien-3-one.

5. A compound according to claim 1 identified as 2,4,4,7-tetramethyl-6,8-nonadien-3-one.

6. A compound according to claim 1 identified as 5-ethyl-8-methyl-7,9-decadien-4-one.

7. A compound according to claim 1 identified as 5-ethyl-8-methyl-7,9-decadien-4-one oxime.

8. A compound according to claim 1 identified as 3,3,6-trimethyl-5,7-octadien-2-one.

9. A compound according to claim 1 identified as 3,3,6-trimethyl-5,7-octadien-2-one oxime.

10. A compound according to claim 1 identified as 2,4,4,7-tetramethyl-6,8-nonadien-3-one oxime.

11. A compound according to claim 1 selected from the group consisting of 2,2-dimethyl-6,8-nonadien-3-one; 2,2-dimethyl-6,8-decadien-3-one; 4,7-dimethyl-6,8-nonadien-3-one; 2,4,4,8-tetramethyl-6,8-nonadien-3-one; 5-isopropyl-2,9-dimethyl-7,9-decadien-4-one and 2,4,4,7,8-pentamethyl-6,8-nonadien-3-one.

12. A compound according to claim 1 identified as 2,4,4-trimethyl-6,8-nonadien-3-one.

13. An alcohol selected from the group consisting of 2,2-dimethyl-6,8-nonadien-3-ol; 3-ethyl-4,7-dimethyl-6,8-nonadien-3-ol; 2,2,7-trimethyl-6,8-nonadien-3-ol; 2,2,3,7-tetramethyl-6,8-nonadien-3-ol; 2,3,4,4,7-pentamethyl-6,8-nonadien-3-ol; 2,2-dimethyl-6,8-decadien-3-ol and 2,4,4,8-tetramethyl-6,8-nonadien-3-ol.

14. A compound according to claim 13 identified as 2,2-dimethyl-6,8-nonadien-3-ol.

15. A compound according to claim 13 identified as 3-ethyl-4,7-dimethyl-6,8-nonadien-3-ol.

16. A compound according to claim 13 identified as 2,2,7-trimethyl-6,8-nonadien-3-ol.

17. A compound according to claim 13 identified as 2,2,3,7-tetramethyl-6,8-nonadien-3-ol.

18. A compound according to claim 13 identified as 2,3,4,4,7-pentamethyl-6,8-nonadien-3-ol.

19. An odorant composition comprising an olfactorily effective amount of a compound of the formula

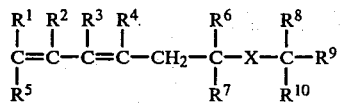

wherein:

(i) X stands for

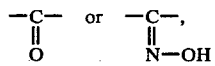

(ii) $R^1$ through $R^{10}$ are alike or different and are selected from the group consisting of hydrogen, methyl, ethyl, n-propyl and isopropyl except that when both $R^6$ and $R^7$ are hydrogen, none of the groups $R^8$, $R^9$ or $R^{10}$ is hydrogen, and (iii) the total number of carbon atoms in the molecule does not exceed fifteen.

and at least one other olfactory ingredient.

20. A composition according to claim 19 where X stands for

21. An odorant composition, according to claim 19 comprising an olfactorily effective amount of 2,4,4-trimethyl-6,8-nonadien-3-one.

22. An odorant composition according to claim 19 comprising an olfactorily effective amount of 2,4,4,7-tetramethyl-6,8-nonadien-3-one.

23. An odorant composition, according to claim 19 comprising an olfactorily effective amount of 2,2,7-trimethyl-6,8-nonadien-3-one.

24. An odorant composition according to claim 19 comprising an olfactorily effective amount of 5-ethyl-8-methyl-7,9-decadien-4-one.

25. An odorant composition according to claim 19 comprising an olfactorily effective amount of 5-ethyl-8-methyl-7,9-decadien-4-one oxime.

26. An odorant composition according to claim 19 comprising an olfactorily effective amount of 3,3,6-trimethyl-5,7-octadien-2-one.

27. An odorant composition according to claim 19 comprising an olfactorily effective amount of 3,3,6-trimethyl-5,7-octadien-2-one oxime.

28. An odorant composition according to claim 19 comprising an olfactorily effective amount of 2,4,4,7-tetramethyl-6,8-nonadien-3-one oxime.

29. An odorant composition comprising an olfactorily effective amount of a compound selected from the group consisting of 2,2-dimethyl-6,8-nonadien-3-ol; 3-ethyl-4,7-dimethyl-6,8-nonadien-3-ol; 2,2,7-trimethyl-6,8-nonadien-3-ol; 2,2,3,7-tetramethyl-6,8-nonadien-3-ol and 2,3,4,4,7-pentamethyl-6,8-nonadien-3-ol.

30. An odorant composition, according to claim 29, comprising an olfactorily effective amount of 2,2-dimethyl-6,8-nonadien-3-ol.

31. An odorant composition, according to claim 29 comprising an olfactorily effective amount of 3-ethyl-4,7-dimethyl-6,8-nonadien-3-ol.

32. An odorant composition according to claim 29 comprising an olfactorily effective amount of 2,2,7-trimethyl-6,8-nonadien-3-ol.

33. An odorant composition, according to claim 29 comprising an olfactorily effective amount of 2,2,3,7-tetramethyl-6,8-nonadien-3-ol.

34. An odorant composition according to claim 29 comprising an olfactorily effective amount of 2,3,4,4,7-pentamethyl-6,8-nonadien-3-ol.

35. A method for improving the odor of fragrance compositions which comprises adding thereto an olfactorily effective amount of a compound of the formula

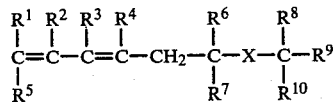

wherein:
(i) stands for

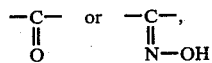

(ii) $R^1$ through $R^{10}$ are alike or different and are selected from the group consisting of hydrogen, methyl, ethyl, n-propyl and isopropyl except that when both $R^6$ and $R^7$ are hydrogen, none of the groups $R^8$, $R^9$ or $R^{10}$ is hydrogen, and
(iii) the total number of carbon atoms in the molecule does not exceed fifteen.

* * * * *